United States Patent [19]

Schmidt et al.

[11] 4,160,794

[45] Jul. 10, 1979

[54] 1-OXO-2,2-[DIALKYLPHOSPHONO(ALKYL)ALKYLOXY]-1,2-DIPHENYLETHANE

[75] Inventors: Andreas Schmidt, Reinach; Rudolf Kirchmayr, Münchenstein, both of Switzerland

[73] Assignee: Ciba-Geigy Corporation, Ardsley, N.Y.

[21] Appl. No.: 867,992

[22] Filed: Jan. 9, 1978

Related U.S. Application Data

[62] Division of Ser. No. 642,230, Dec. 19, 1975, Pat. No. 4,082,821.

[30] Foreign Application Priority Data

Dec. 24, 1974 [CH] Switzerland .................... 017285/74
Dec. 26, 1975 [CH] Switzerland .................... 015304/75

[51] Int. Cl.² ............................................ C07F 9/40
[52] U.S. Cl. .............................. 260/927 R; 260/932
[58] Field of Search ......................... 260/932, 927 R

[56] References Cited

U.S. PATENT DOCUMENTS

| 3,715,293 | 2/1973 | Sandner et al. ................. 204/159.14 |
| 3,829,534 | 8/1974 | Dickert, Jr. et al. ......... 260/970 OR |
| 3,998,712 | 12/1976 | Hickmann et al. .............. 204/159.15 |

FOREIGN PATENT DOCUMENTS

1390006 4/1975 United Kingdom ............... 204/159.14

*Primary Examiner*—Anton H. Sutto
*Attorney, Agent, or Firm*—Luther A. R. Hall

[57] ABSTRACT

Benzoin derivatives which contain one or two phosphonoalkyl groups are suitable photoinitiators for the photopolymerization of unsaturated compounds, for example for curing printing inks or coatings of acrylates or unsaturated polyester resins. The new compounds can be obtained in different ways, for example by the Arbuzov reaction from the corresponding haloalkyl derivatives or by addition of esters of unsaturated phosphonic acids to benzoin or benzoin ethers.

9 Claims, No Drawings

1-OXO-2,2-[DIALKYLPHOSPHONO(ALKYL)AL-KYLOXY]-1,2-DIPHENYLETHANE

This is a divisional of application Ser. No. 642,230 filed on Dec. 19, 1975, now U.S. Pat. No. 4,082,821, issued Apr. 4, 1978.

The invention relates to new phosphonates which are derivatives of benzoin, and also to their use as initiators for the photopolymerisation of unsaturated polymerisable systems.

It is known that unsaturated monomers or mixtures thereof with unsaturated polymers in the presence of suitable initiators, for example carbonyl compounds which contain a halogen in α-position to the carbonyl group, mercaptans, aromatic disulphides, nitroso compounds, azo compounds, benzoins and benzoin ethers, can be polymerised photochemically. There is a need in the art for initiators which have a good storage life in the dark and initiate the polymerisation more rapidly and at the same time produce a higher polymer yield per unit of time than is possible with the initiators that have been disclosed so far. By using such improved photoinitiators it would be possible to make more economic use of the costly industrial ultra-violet exposure apparatus.

The present invention accordingly provides compounds which, in surprisingly advantageous manner, are suitable for use as initiators for the photopolymerisation of polymerisable systems that contain unsaturated compounds. The advantage of these compounds resides primarily in a more rapid start of the photopolymerisation and a higher time yield as a consequence thereof, while at the same time possessing an excellent storage life in the dark. A further advantage is that the compounds are in liquid or in readily soluble crystalline form, so that they can be easily incorporated.

The compounds of the present invention have the formula

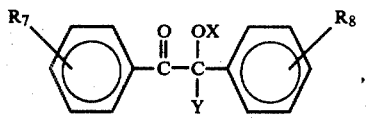

(I)

wherein

X represents hydrogen, alkyl of 1 to 4 carbon atoms, hydroxyalkyl of 2 to 3 carbon atoms, haloalkyl of 2 to 3 carbon atoms, alkoxyalkyl of 3 to 8 carbon atoms, alkenyl of 3 to 4 carbon atoms, cycloalkyl of 5 to 7 carbon atoms, aralkyl of 7 to 8 carbon atoms, 2-tetrahydrofuranyl, 2-tetrahydropyranyl, 2-(6-methoxy)tetrahydropyranyl, phenyl or substituted phenyl or a phosphonoalkyl group of formula $-(CH_2)_n-P(O)(OR_1)(OR_2)$, Y represents hydrogen, alkyl of 1 to 4 carbon atoms, alkenyl of 3 to 4 carbon atoms, cycloalkyl of 5 to 7 carbon atoms, aralkyl of 7 to 8 carbon atoms, phenyl or substituted phenyl or a phosphonoalkyl group of formula $-CH(R_5)-CH(R_6)-P(O)(OR_3)(OR_4)$ or a phosphonoalkoxy group of formula $-O-(CH_2)_n-P(O)(OR_3)(OR_4)$, each of $R_1$, $R_2$, $R_3$ and $R_4$ independently represents alkyl of 1 to 4 carbon atoms, haloalkyl of 2 to 3 carbon atoms, alkoxyalkyl of 3 to 8 carbon atoms, cycloalkyl of 5 to 7 carbon atoms, aralkyl of 7 to 8 carbon atoms, or phenyl or substituted phenyl, or $R_1$ and $R_2$ together, or $R_3$ and $R_4$ together, represent a branched or unbranched alkyl radical of 2 to 7 carbon atoms, each of $R_5$ and $R_6$ independently represents hydrogen, alkyl of 1 to 4 carbon atoms or phenyl, each of $R_7$ and $R_8$ independently represents hydrogen, alkyl or alkoxy of 1 to 4 carbon atoms, halogen or phenyl and n is 2 or 3, with the proviso that at least one of the radicals X and Y represents a phosphonoalkyl or phosphonoalkoxy group as defined herein, and with the further proviso that when Y is a phosphonoalkoxy group, X is a phosphonoalkyl group.

Alkyl of 1 to 4 carbon atoms represented by X, Y, $R_1$, $R_2$, $R_3$, $R_4$, $R_5$, $R_6$, $R_7$ and $R_8$ can be methyl, ethyl, propyl, isopropyl, butyl, sec. butyl or tert. butyl.

Where X represents hydroxyalkyl of 2 to 3 carbon atoms it can be hydroxyethyl or hydroxypropyl.

Haloalkyl of 2 to 3 carbon atoms represented by X, $R_1$, $R_2$, $R_3$ or $R_4$ can be, for example, 2-chloroethyl, 2,3-dibromopropyl or 2-bromoethyl. Alkoxyalkyl of 3 to 8 carbon atoms represented by X, $R_1$, $R_2$, $R_3$ or $R_4$ can be, for example, 1-methoxyethyl, 2-ethoxyethyl, 1-propoxyethyl, 2-isopropoxyethyl, 1- or 2-butyloxyethyl, 2- or 3-ethoxypropyl or 2-hexyloxyethyl.

A branched or an unbranched alkylene radical represented by $R_1$ and $R_2$ together or $R_3$ and $R_4$ together can be, for example, 1,2-ethylene, 1,2-propylene, 1,3-propylene, 2,2-dimethyl-1,3-propylene or 2,2-diethyl-1,3-propylene.

Alkenyl of 3 to 4 carbon atoms represented by X or Y can be allyl, methallyl or butenyl.

Cycloalkyl of 5 to 7 carbon atoms represented by X, Y, $R_1$, $R_2$, $R_3$ or $R_4$ can be, for example, cyclopentyl, cyclohexyl or methylcyclohexyl.

Aralkyl of 7 to 8 carbon atoms represented by X, Y, $R_1$, $R_2$, $R_3$ or $R_4$ can be benzyl, methylbenzyl or phenylethyl.

A substituted phenyl group represented by X, Y, $R_1$, $R_2$, $R_3$ or $R_4$ can be, for example, halogenophenyl, alkylphenyl or alkoxyphenyl.

Preferred compounds are those of formula I wherein (a) Y represents a phosphonoethyl group $-CH_2-CH_2-P(O)(OR_3)(OR_4)$, in particular those in which X represents alkyl of 1 to 4 carbon atoms, haloalkyl of 2 to 3 carbon atoms, alkoxyalkyl of 3 to 8 carbon atoms, aralkyl of 7 to 8 carbon atoms or phenyl, and $R_7$ and $R_8$ represent hydrogen, (b) X represents a phosphonoalkyl group, primarily those compounds wherein X represents a phosphonoethyl group, Y represents hydrogen, alkyl of 1 to 4 carbon atoms or a phosphonoethyl group, and $R_7$ and $R_8$ represent hydrogen, (c) X represents a phosphonoalkyl group and Y represents a phosphonoalkoxy group, in particular those wherein X represents a phosphonoethyl group and Y represents a phosphonoethoxy group, and $R_5$, $R_6$, $R_7$ and $R_8$ represent hydrogen.

In each of these subclasses, preferred compounds are those wherein $R_1$, $R_2$, $R_3$ and $R_4$ represent an alkyl radical of 1 to 4 carbon atoms, an alkoxyethyl radical of 3 to 6 carbon atoms or a halogenoethyl radical, or $R_3$ and $R_4$ together represent a branched alkylene radical of 3 to 6 carbon atoms.

The following compounds are examples of phosphonates of formula I:

1-oxo-2-(2-dimethylphosphonoethoxy)-1,2-diphenylethane
1-oxo-2-(2-diethylphosphonoethoxy)-1,2-diphenylethane
1-oxo-2-(2-diisopropylphosphonoethoxy)-1,2-diphenylethane
1-oxo-2-(2-dibutylphosphonoethoxy)-1,2-diphenylethane
1-oxo-2-(2-di-β-chloroethylphosphonoethyloxy)-1,2-diphenylethane
1-oxo-2-(2-diethylphosphonoethoxy)-1,2,2-triphenylethane
1-oxo-2-(2-dimethylphosphonoethoxy)-2-methyl-1,2-diphenylethane
1-oxo-2-(2-diethylphosphonoethoxy)-2-methyl-1,2-diphenylethane
1-oxo-2-(2-diethylphosphonoethoxy)-2-ethyl-1,2-diphenylethane
1-oxo-2-(2-diethylphosphonoethoxy)-2-(2-diethylphosphonoethyl)-1,2-diphenylethane
1-oxo-2-(2-diethylphosphonoethoxy)-1-(4-chlorophenyl)-2-phenyl-ethyne
1-oxo-2-(2-diethylphosphonoethoxy)-1,2-di-(4-chlorophenyl)-2-phenyl-ethane
1-oxo-2-(3-diethylphosphonopropoxy)-1,2-diphenylethane
1-oxo-2-(3-diethylphosphonopropoxy)1,2-di-(4-methylphenyl)-ethane
1-oxo-2-(3-diethylphosphonopropoxy)-1,2-di-(4-methoxyphenyl)-ethane
1-oxo-2-methoxy-2-(2-dimethylphosphonoethyl)-1,2-diphenylethane
1-oxo-2-methoxy-2-(2-diethylphosphonoethyl)-1,2-diphenylethane
1-oxo-2-ethoxy-2-(2-diethylphosphonoethyl)-1,2-diphenylethane
1-oxo-2-isopropoxy-2-(2-diethylphosphonoethyl)-1,2-diphenylethane
1-oxo-2-butoxy-2-(2-diethylphosphonoethyl)-1,2-diphenylethane
1-oxo-2-(2-chloroethoxy)-2-(2-diethylphosphonoethyl)-1,2-diphenylethane
1-oxo-2-methoxy-2-(2-diisopropylphosphonoethyl)-1,2-diphenylethane
1-oxo-2-methoxy-2-(2-dibutylphosphonoethyl)-1,2-diphenylethane
1-oxo-2-methoxy-2-(2-diphenylphosphonoethyl)-1,2-diphenylethane
1-oxo-2-methoxy-2-(2-di-β-chloroethyl-phosphonoethyl)-1,2-diphenylethane
1-oxo-2-(1-methoxyethoxy)-2-(2-dimethylphosphonoethyl)-1,2-diphenylethane
1-oxo-2-(1-butyloxyethoxy)-2-(2-dimethylphosphonoethyl)-1,2-diphenylethane
1-oxo-2-(2-tetrahydrofuryl)-2-(2-di-β-methoxyethylphosphonoethyl)-1,2-diphenylethane
1-oxo-2-(2-tetrahydropyranyl)-2-(2-diethylphosphonoethyl)-1,2-diphenylethane
1-oxo-2,2-di-(2-dimethylphosphonoethoxy)-1,2-diphenylethane
1-oxo-2,2-di-(2-diethylphosphonoethoxy)-1,2-diphenylethane
1-oxo-2,2-di-(2-dibutylphosphonoethoxy)-1,2-diphenylethane
1-oxo-2,2-di-(3-diethylphosphonopropyloxy)-1,2-diphenylethane The phosphonates of the present invention can be manufactured in different ways. For example, compounds of formula I, in which X represents a phosphonoalkyl radical, is obtained from haloalkyl ether of benzoin, of from α-alkylbenzoins, by reaction with trialkylphosphites, as is illustrated by the following reaction equation

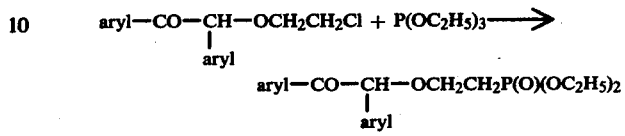

Instead of trialkylphosphites, it is also possible to use the alkali compounds of dialkylphosphites.

Compounds of formula I, in which Y represents a phosphonoalkyl radical, can be obtained by addition of esters of unsaturated phosphonic acids, in particular of vinylphosphonic acid, to benzoin ether in the presence of alkali catalysts, as is illustrated by the following example:

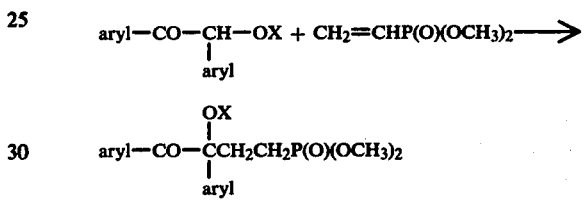

If X is a phosphonoalkyl radical, diphosphonates are obtained.

Compounds of formula I, in which X represents a phosphonoalkyl radical and Y represents a phosphonoalkoxy radical, can be obtained for example from 1,1-di(haloalkyl)acetals of benzoin by reaction with phosphites, as is illustrated by the following example:

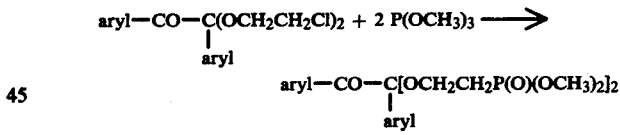

The phosphonates of the present invention can be used as initiators for the photopolymerisation of polymerisable systems which contain unsaturated compounds. Such systems are, for example, unsaturated monomers, for example the methyl, ethyl, n- or tert. butyl, isooctyl or hydroxyethyl esters of acrylic acid, methacrylic acid alkyl esters, such as methyl methacrylate or ethyl methacrylate, di-(meth)-acrylates of aliphatic diols or polyols, trimethylolpropane trisacrylate, pentaerythritol tetracrylate, pentaerythritol trisacrylate, acrylonitrile, methacrylic nitrile, acrylic amide, methacrylic amide, N,N-disubstituted acrylic amides and methacrylic amides, vinyl acetate, vinyl acrylate, vinyl propionate, succinic acid divinyl ester, isobutyl vinyl ether, butanediol-1,4-divinyl ester, styrene, alkylstyrenes, halogenostyrenes, divinyl benzenes, vinyl naphthalene, N-vinylpyrrolidone, vinyl chloride, vinylidene chloride, diallyl phthalate, diallyl maleate, triallyl isocyanurate, triallyl phosphate, ethylene glycol diallyl ether, pentaerythritol tetrallyl ether and mixtures of such monomers.

Photopolymerisable systems are also unsaturated oligomers or polymers and mixtures thereof with unsaturated monomers. Comprised among these are above all the mixtures of unsaturated polymers with unsaturated monomers. By unsaturated polyesters are meant, for example, the polycondensation products of $\alpha,\beta$-unsaturated dicarboxylic acids or derivatives thereof with polyols. Examples of $\alpha,\beta$-unsaturated dicarboxylic acids or derivatives thereof are maleic acid, maleic anhydride, fumaric acid, mesaconic acid, citraconic acid. Besides the unsaturated dicarboxylic acids, saturated or non-polymerisable dicarboxylic acids can also be incorporated in order to select the degree of unsaturation, for example succinic acid, sebacic acid, isophthalic acid, phthalic acid, halogenated phthalic acids or 3,6-endomethylene-$\Delta^4$-tetrahydrophthalic acid, as well as the anhydrides of these dicarboxylic acids.

Principally glycols, for example ethylene glycol, propanediol-, 2-diethylene glycol, 1,3-propylene glycol, 1,4-tetramethylene glycol and also triethylene glycol, are used as polyols for the manufacture of the polycondensation products.

Further modifications of the unsaturated polyester resins are possible through the incorporation of monocarboxylic acids or monoalcohols.

These unsaturated polyesters are normally used in admixture with unsaturated monomers which contain allyl or vinyl groups, preferably with styrene. Such mixtures can be photopolymerised after addition of phosphonates of formula I in advantageous manner to give moulding or coating compounds.

Moulding compounds which can be photopolymerised with compounds of formula I are, for example, air-drying moulding compounds. These are unsaturated polyesters which, in addition to $\alpha,\beta$-unsaturated dicarboxylic acid radicals, also contain $\beta,\gamma$-unsaturated ether radicals.

Coating compounds which can be photopolymerised with compounds of formula I are, for example, coatings of unsaturated monomers and unsaturated polymers. These varnishes can also be photopolymerised by the "activated surface process," wherein the coating compound is applied with the photoinitiator to a peroxide-containing layer which has been applied beforehand to the substrate and subsequently photopolymerised.

The photopolymerisable compounds or mixtures can be stabilised by adding the conventional thermal inhibitors used in the manufacture of light-sensitive compounds. Examples thereof are hydroquinone, p-quinone, p-methoxyphenol, $\beta$-naphthylamine, $\beta$-naphthol and phenols. The photopolymerisable compounds or mixtures can also contain chain transfer agents, such as triethanolamine or cyclohexene.

In order to eliminate the inhibiting action of atmospheric oxygen, it is advantageous to add paraffins, waxes or wax-like substances to the coating compounds with the photoinitiators. These float at the onset of the polymerisation and so prevent the inhibiting action of atmospheric oxygen.

Another possibility of preventing the inhibiting action of atmospheric oxygen consists in carrying out the reaction in an atmosphere of inert gas, or in adding UV-permeable fillers, for example specific silicates, to the polyester resin. The filled compounds also harden rapidly in the presence of air under ultra-violet irradiation, because the amount of binder at the surface is reduced.

The introduction of autoxidisable groups into the resin to be cured can also eliminate the inhibiting action of atmospheric oxygen. For example, this can be accomplished by copolymerisation with certain allyl compounds.

It is also possible to add small amounts of ultraviolet absorbers to the moulding and coating compounds without the reactivity of the photosensitisers being substantially impaired.

The coating and moulding compounds can also be formulated with small amounts of conventional carriers and fillers, for example glass fibres, synthetic fibres, silica and talcum as well as with thixotropic agents.

The phosphonates of the present invention can furthermore be used for the manufacture of photopolymerisable elements from which, after exposure and by washing out, relief moulds for printing purposes can be obtained. Linear synthetic polyamides are particularly suitable as unsaturated polymers in photopolymerisable layers for obtaining relief moulds for printing purposes. Photopolymerisable unsaturated monomers which are used in the cited polymers in light-sensitive layers for obtaining relief moulds are preferably those that contain at least two polymerisable olefinic double bonds, and, in addition to the double bonds, amide groups, for example methylene-bis-acrylic amide, methylene-bis-methacrylic amide and also bis-acrylic or bis-methacrylic amides of diamines.

A further use of the compounds of formula I as photoinitiator is in the drying of printing inks which contain unsaturated monomers and unsaturated polymers as binders, by ultra-violet irradiation. On the basis of binders with, for example, conjugated double bonds, it is possible to prepare printing inks which dry in a short space of time under the action of ultra-violet rays.

Examples of such binders are natural or synthetic conjugated oils, unsaturated polyester resins or polyfunctional acrylates or methacrylates. Such printing ink binders frequently contain as additives chain transfer agents, for example triethanolamine or cyclohexene or stabilisers, such ad diethylhydroxylamine. The phosphonates of the present invention are particularly suitable initiators for the photochemical curing of such printing ink binders.

The compounds of formula I are used for the fields of application referred to in amounts of 0.1 to 20 percent by weight, preferably of about 0.5 to about 10 percent by weight, either by themselves or in admixture with each other.

The addition of the initiators to the photopolymerisable systems is effected as a rule by simply stirring them in, since most of the systems are liquid. Generally, a solution of the photocurers of the present invention is obtained, so that their homogeneous distribution and the transparency of the polymers is ensured.

The polymerisation of the systems sensitised in such a way is carried out by the known methods of photopolymerisation by irradiation with light that is rich in shortwave radiation. Suitable light sources for the irradiation of the substrates containing the photoinitiators of formula I are mercury medium pressure, high pressure and low pressure irradiators, and also superactinic fluorescent tubes whose emission spectra are in the range between 300 and 400 m$\mu$.

The following Examples describe the manufacture and use of the phosphonates in more detail, the parts being by weight.

EXAMPLE 1

16.4 g. (0.1 mole) of benzoin methyl ether are dissolved in 100 ml of dimethyl sulphoxide. While passing in nitrogen, 3 ml of 4 normal sodium hydroxide solution are added dropwise. Then 18 g (0.11 mole) of diethyl vinylphosphonate are added dropwise in the course of

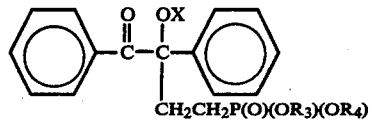

|           |                                          |                                                    |                                                    |      | ultimate analysis |       |       |       |      |       |
|-----------|------------------------------------------|----------------------------------------------------|----------------------------------------------------|------|-------|-------|-------|-------|------|-------|
|           |                                          |                                                    |                                                    |      | C     |       | H     |       | P    |       |
| initiator | X                                        | $R_3$                                              | $R_4$                                              | m.p. | calc. | found | calc. | found | calc.| found |
| 4         | $-CH_2CH_2O-CH_3$                        | $C_2H_5$                                           | $C_2H_5$                                           | —    |       |       |       |       | 7.13 | 7.1   |
| 5         | $-C_6H_5$ (phenyl)                       | $C_2H_5$                                           | $C_2H_5$                                           | 121° |       |       |       |       |      |       |
| 6         | cyclohexyl                               | $C_2H_5$                                           | $C_2H_5$                                           |      | 65.23 | 65.39 | 7.18  | 7.33  | 6.72 | 6.3   |
| 7         | $-CH_3$                                  | $CH_3$                                             | $CH_3$                                             |      | 62.98 | 63.20 | 6.40  | 6.60  | 8.55 | 8.2   |
| 8         | $-CH_3$                                  | $-CH_2-C(CH_3)_2-CH_2-$                            |                                                    | 208° | 65.68 | 65.29 | 6.72  | 6.80  | 7.71 | 7.7   |
| 9         | $-CH_3$                                  | $CH_2CH_2OCH_3$                                    | $CH_2CH_2OCH_3$                                    |      | 61.32 | 61.30 | 6.93  | 7.1   | 6.87 | 6.7   |
| 10        | $-CH_3$                                  | $C_4H_9$                                           | $C_4H_9$                                           |      |       |       |       |       | 6.94 | 7.3   |
| 11        | $-C_2H_5$                                | $CH_2CH_2OCH_3$                                    | $CH_2CH_2OCH_3$                                    |      | 62.06 | 62.4  | 7.16  | 7.2   | 6.67 | 6.5   |
| 12        | $-C_2H_5$                                | $CH_2CH_2Cl$                                       | $CH_2CH_2Cl$                                       |      |       |       |       |       | 6.54 | 6.27  |
| 13        | $-CH(CH_3)_2$                            | $CH_3$                                             | $CH_3$                                             |      |       |       |       |       | 7.94 | 7.52  |
| 14        | $-CH(CH_3)_2$                            | $C_4H_9$                                           | $C_4H_9$                                           |      |       |       |       |       | 6.53 | 7.1   |
| 15        | $-CH(CH_3)_2$                            | $CH_2CH_2OCH_3$                                    | $CH_2CH_2OCH_3$                                    |      | 62.73 | 63.2  | 7.37  | 7.4   | 6.47 | 6.4   |
| 16        | $-CH_2CH_2Cl$                            | $C_2H_5$                                           | $C_2H_5$                                           |      |       |       |       |       | 6.85 | 6.8   |
| 17        | $-C_2H_5$                                | $CH_3$                                             | $CH_3$                                             |      | 63.82 | 64.3  | 6.70  | 6.9   | 8.23 | 7.8   |

10 minutes. The reaction mixture is stirred for 16 hours at room temperature under nitrogen and subsequently neutralised with 2 normal hydrochloric acid. After the reaction mixture has been completely concentrated under reduced pressure, the oily residue is taken up in toluene, washed twice with water and again completely concentrated by rotary evaporation to yield 1-oxo-2-(2-diethylphosphonoethyl)-2-methoxy-1,2-diphenylethane as a slightly viscous yellowish oil which crystallises on standing; m.p. 60°-62° C. (initiator 1).

EXAMPLE 2

The procedure of Example 1 is repeated using the equivalent amount of benzoin isopropyl ether instead of benzoin methyl ether, to yield 1-oxo-2-isopropoxy-2-(2-diethylphosphonoethyl)-1,2-diphenylethane of $n_D^{20} = 1.5318$ (initiator 2).

EXAMPLE 3

The procedure of Example 1 is repeated using the equivalent amount of benzoin ethyl ether instead of benzoin methyl ether, to yield 1-oxo-2-ethoxy-2-(2-diethylphosphonoethyl)-1,2-diphenylethane which melts at 75° C.

EXAMPLE 4

The procedure of Example 1 is repeated using the equivalent amount of another benzoin ether of formula $C_6H_5-CO-CH(OX)-C_6H_5$ instead of benzoin methyl ether and reacting it with a vinylphosphonate of formula $CH_2=CH-P(O)(OR_3)(OR_4)$, to yield the compounds listed in the following table of formula

EXAMPLE 5

27.5 g (0.1 mole) of 2-chloroethyl benzoin ether and 37.5 g (0.15 mole) of tributylphosphite are stirred for 4 hours at 175° C. and butyl chloride distills off (b.p. 78° C.). Excess tributyl phosphite is distilled off by applying a water-jet and subsequently a high vacuum (0.01 Torr). The residue is purified in a silica gel column (eluant: toluene/methanol 9:9). Rf = 0.35.

2-Dibutyl-phosphonoethyl benzoin ether is obtained as a yellowish oil of the following basic composition:

| $C_{calc}$: | 66.65 % | $H_{calc}$: | 7.69 % | $P_{calc}$: | 7.16 % |
|---|---|---|---|---|---|
| $C_{found}$: | 66.4 % | $H_{found}$: | 7.8 % | $P_{found}$: | 6.9 % |
| (Initiator 18). | | | | | |

EXAMPLE 6

The procedure of Example 5 is repeated using the equivalent amount of triethylphosphite instead of tributylphosphite and heating only to 160° C. to yield 2-diethylphosphonoethyl benzoin ether as a yellowish oil of the following composition:

| $C_{calc}$: | 63.82 % | $H_{calc}$: | 6.70 % | $P_{calc}$: | 8.23 % |
|---|---|---|---|---|---|
| $C_{found}$: | 64.05 % | $H_{found}$: | 7.02 % | $P_{found}$: | 8.16 % |
| (Initiator 19). | | | | | |

EXAMPLE 7

70.6 (0.2 mole) of benzil-di(2-chloroethyl)ketal and 99.6 g (0.6 mole) of triethylphosphite are heated together, with stirring, for 16 hours to 160° C. Excess triethylphosphite is distilled off subsequently under reduced pressure and the residue is purified in a silica gel column with toluene/methanol 9:1 as eluant, to yield two fractions. Fraction 1 consists of benzil-(2-diethylphosphonoethyl)-(2-chloroethyl)ketal as a yellowish oil of the following basic composition:

| | | | | |
|---|---|---|---|---|
| $Cl_{calc}$: | 7.79 % | $P_{calc}$: | 6.81 % | |
| $Cl_{found}$: | 7.71 % | $P_{found}$: | 6.85 % | |
| (Initiator 20). | | | | |

Fraction 2 consists of benzil-bis(2-diethylphosphonoethyl)ketal, which is also a yellowish oil of the following basic composition:

| | | | | | |
|---|---|---|---|---|---|
| $C_{calc}$: | 56.11 % | $H_{calc}$: | 6.88 % | $P_{calc}$: | 11.13 % |
| $C_{found}$: | 56.50 % | $H_{found}$: | 6.97 % | $P_{found}$: | 11.05 % |
| (Initiator 21). | | | | | |

EXAMPLE 8

0.1 g of different known photoinitiators and photoinitiators of the present invention is dissolved in 10 g of freshly distilled methyl acrylate. This solution is irradiated with a mercury vapour high pressure lamp in a thermostabilised water bath of 25° C. in a quartz glass tube. The lamp is at a distance of 10 cm from the quartz tube. Before the irradiation, nitrogen is passed through the solution of the initiator for 1 minute and this passage of nitrogen is also continued during the irradiation. The polymerisation of the monomer which commences during the irradiation is signalled by a rise in temperature of the irradiated solution. The exposure time up to the rise in temperature in the solution is rated as the starting time. The exposure time is 20 seconds. Immediately after the irradiation, the solution is cooled in order to prevent a thermal polymerisation. The solution of the resultant polymer in the monomer is rinsed in a round flask with small amounts of ethyl acetate and the solvent and non-polymerised monomer are distilled off by rotary evaporation. The polymeric residue is dried in a vacuum cabinet at 50°–60° C. and then weighed.

The amounts of polyacrylic acid methyl ester obtained with different initiators by performing the experiment described above are reported in Table A.

Table A

| amount of initiator in percent by weight | starting time in seconds | amount of polyacrylic acid, methyl ester obtained in percent by weight |
|---|---|---|
| 1% of benzoin | 5 | 6.5 |
| 1 % by benzoin isopropyl ether | 4 | 7.7 |
| 1 % of initiator 1 | 3 | 12 |
| 1 % of initiator 2 | 6 | 5 |
| 1 % of initiator 3 | 8 | 6 |
| 1 % of initiator 4 | 4 | 10 |
| 1 % of initiator 5 | 9 | 4 |
| 1 % of initiator 6 | 4 | 8 |
| 1 % of initiator 7 | 5 | 6 |
| 1 % of initiator 8 | 6 | 8 |
| 1 % of initiator 9 | 5 | 8 |
| 1 % of initiator 10 | 5 | 9 |
| 1 % of initiator 11 | 11 | 5 |
| 1 % of initiator 12 | 6 | 8 |
| 1 % of initiator 13 | 3 | 5.6 |
| 1 % of initiator 14 | 13 | 3 |
| 1 % of initiator 15 | 14 | 3 |
| 1 % of initiator 18 | 14 | 5 |
| 1 % of initiator 19 | 5 | 9 |
| 1 % of initiator 20 | 3 | 10 |

Table A-continued

| amount of initiator in percent by weight | starting time in seconds | amount of polyacrylic acid, methyl ester obtained in percent by weight |
|---|---|---|
| 1 % of initiator 21 | 4 | 10 |

Without photoinitiator the amount of polymerisation is below 0.1%. It is evident from the figures reported in Table A that the photoinitiators of the present invention initiate the polymerisation more rapidly and give higher polymer yields than known photoinitiators.

EXAMPLE 9

0.2 Part by weight of known photoinitiators and photoinitiators of the present invention is incorporated in unsaturated polyester resin as follows:

10 parts of unsaturated polyester resin (polyester based on maleinate with a styrene content of 35%)
0.2 part of photoinitiator
0.1 part of a 10% solution of paraffin in toluene.

This mixture is stirred until a solution is obtained, which is then drawn out on glass plates with a film drawer (500μ). The films are irradiated with a fluorescent lamp of high ultraviolet concentration at a distance of 5 cm. After an exposure time of 20 minutes, the hardness of the films is determined with a pendulum device (pendulum hardness according to König). The results of this experiment are reported in the following table:

Table B

| initiator | pendulum hardness (Konig) after an exposure time of 20 minutes |
|---|---|
| benzoin | 55 |
| initiator 1 | 70 |

EXAMPLE 10

0.2 Part by weight of known photoinitiators and photoinitiators of the present invention is incorporated in trismethylolpropane trisacrylate as follows:

10 parts of trismethylolpropane trisacrylate
0.2 part of photoinitiator
0.1 part of a 10% solution of paraffin in toluene This mixture is stirred until a solution is obtained, which is then drawn out on glass plates with a film drawer (200μ). The plates are irradiated with a fluorescent tube of high ultraviolet concentration at a distance of 5 cm. After an exposure time of 5 minutes, the hardness of the films is determined with a pendulum device (pendulum hardness according to Konig). The results of this experiment are reported in Table C:

Table C

| initiator | pendulum hardness (Konig) after 5 minutes exposure |
|---|---|
| benzoinisopropylether | 63 |
| initiator 1 | 65 |

Without initiator, the acrylate film remains fluid after 5 minutes exposure.

EXAMPLE 11

A 2% solution of known photoinitiators and a photoinitiators of the present invention in unsaturated polyester resin (polyester on maleinate basis with a styrene content of 35%) is prepared at 25° C. This solution is stored in the dark at 60° C. and examined daily. The number of days until solidification of the solution is determined. Polyester resin which contains no additive is simultaneously tested for comparison purposes. The results of the experiment are reported in Table D.

Table D

| photoinitiator | number of days until solidifications |
|---|---|
| polyester resin without additive | 18 |
| benzoin | 1 |
| benzoin isopropyl ether | 11–12 |
| initiator 1 | 19–20 |

We claim:
1. A compound of formula I

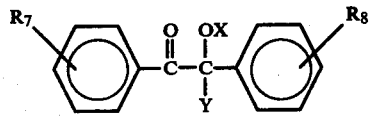

wherein
x represents a phosphonoalkyl group of formula

—(CH$_2$)$_n$P(O)(OR$_1$)(OR$_2$);

Y represents a phosphonoalkyl group of the formula

—CH(R$_5$)—CH(R$_6$)—P(O)(OR$_3$)(OR$_4$)

or a phosphonoalkoxy group of formula

—O—(CH$_2$)$_n$P(O)(OR$_3$)(OR$_4$);

each of R$_1$, R$_2$, R$_3$ and R$_4$ independently represents alkyl of 1 to 4 carbon atoms, haloalkyl of 2 to 3 carbon atoms, alkoxyalkyl of 3 to 8 carbon atoms, cycloalkyl of 5 to 7 carbon atoms, aralkyl of 7 to 8 carbon atoms, phenyl, halogeneophenyl, alkylphenyl or alkoxyphenyl, or R$_1$ and R$_2$ together, or R$_3$ and R$_4$ together, represent a branched or unbranched alkylene of 2 to 7 carbon atoms;

each of R$_5$ and R$_6$ independently represents hydrogen, alkyl of 1 to 4 carbon atoms or phenyl;

each of R$_7$ and R$_8$ independently represents hydrogen, alkyl of 1 to 4 carbon atoms, alkoxy of 1 to 4 carbon atoms, halogen or phenyl; and n is 2 or 3.

2. A compound according to claim 1 wherein x represents a phosphonoalkyl group of formula —(CH$_2$)$_n$-P(O)(OR$_1$)(OR$_2$); Y represents a phosphonoalkyl group of formula —CH(R$_5$)—CH(R$_6$)—P(O)(OR$_3$)(OR$_4$) or a phosphonoalkoxy group of formula —O—(CH$_2$)$_n$—P(O)(OR$_3$)(OR$_4$); each of R$_1$, R$_2$, R$_3$ and R$_4$ independently represent alkyl of 1 to 4 carbon atoms, haloalkyl of 2 to 3 carbon atoms, alkoxyalkyl of 3 to 8 carbon atoms, cycloalkyl of 5 to 7 carbon atoms, aralkyl of 7 to 8 carbon atoms, phenyl, halogenophenyl, alkylphenyl or alkoxyphenyl; each of R$_5$ and R$_6$ independently represents hydrogen, alkyl of 1 to 4 carbon atoms or phenyl; each of R$_7$ and R$_8$ independently represents hydrogen, alkyl of 1 to 4 carbon atoms, alkoxy of 1 to 4 carbon atoms, halogen or pehnyl; and n is 2 or 3.

3. A compound according to claim 1 wherein R$_5$ and R$_6$ are each hydrogen.

4. A compound according to claim 1 wherein n is 2, y is —CH$_2$CH$_2$P(O)(OR$_3$)(OR$_4$) and R$_7$ and R$_8$ represent hydrogen.

5. A compound according to claim 4 wherein R$_1$ and R$_2$ represents alkyl of 1 to 4 carbon atoms, alkoxyethyl of 3 to 6 carbon atoms or halogenoethyl.

6. A compound according to claim 1 wherein y represents a phosphonoalkoxy group.

7. A compound according to claim 6 wherein n is 2 and R$_7$ and R$_8$ represent hydrogen.

8. A compound according to claim 1 wherein R$_1$, R$_2$, R$_3$ and R$_4$ represent alkyl of 1 to 4 carbon atoms or halogenoethyl, 9. A compound according to claim 1, 1-oxo-2,2-bis-(2-diethylphosphonoethoxy)-1,2-diphenylethane.

* * * * *